(12) United States Patent
Wu

(10) Patent No.: US 10,537,434 B2
(45) Date of Patent: Jan. 21, 2020

(54) INTERVERTEBRAL IMPLANT

(71) Applicant: Jau-Ching Wu, Taipei (TW)

(72) Inventor: Jau-Ching Wu, Taipei (TW)

( * ) Notice: Subject to any disclaimer, the term of this patent is extended or adjusted under 35 U.S.C. 154(b) by 64 days.

(21) Appl. No.: 15/230,993

(22) Filed: Aug. 8, 2016

(65) Prior Publication Data

US 2018/0036132 A1 Feb. 8, 2018

(51) Int. Cl.
*A61F 2/44* (2006.01)
*A61F 2/30* (2006.01)

(52) U.S. Cl.
CPC ...... *A61F 2/44* (2013.01); *A61F 2002/30069* (2013.01); *A61F 2002/4475* (2013.01); *A61F 2220/0016* (2013.01)

(58) Field of Classification Search
CPC .................................. A61F 2/442; A61F 2/44
USPC ............................................ 623/17.13, 17.15
See application file for complete search history.

(56) References Cited

U.S. PATENT DOCUMENTS

| | | | | |
|---|---|---|---|---|
| 5,002,576 A * | 3/1991 | Fuhrmann | ................ | A61F 2/441 606/247 |
| 5,360,430 A * | 11/1994 | Lin | ........................... | A61F 2/44 606/247 |
| 5,534,029 A * | 7/1996 | Shima | ....................... | A61F 2/44 606/247 |
| 5,562,473 A * | 10/1996 | Ikeya | .................... | H05K 7/1023 439/331 |
| 5,645,599 A * | 7/1997 | Samani | ............... | A61B 17/7062 606/248 |
| 5,755,796 A * | 5/1998 | Ibo | ......................... | A61F 2/4425 606/247 |
| 6,066,175 A * | 5/2000 | Henderson | ................ | A61F 2/44 623/17.11 |
| 6,475,219 B1 * | 11/2002 | Shelokov | ................ | A61B 17/70 606/281 |
| 6,743,257 B2 * | 6/2004 | Castro | ..................... | A61F 2/442 623/17.16 |
| 7,320,708 B1 * | 1/2008 | Bernstein | ................... | A61F 2/44 623/17.15 |
| 7,578,849 B2 * | 8/2009 | Trieu | ..................... | A61F 2/442 606/248 |
| 8,057,549 B2 * | 11/2011 | Butterman | ......... | A61B 17/1671 623/17.13 |
| 8,070,817 B2 * | 12/2011 | Gradl | ....................... | A61F 2/44 623/17.15 |
| 8,187,332 B2 | 5/2012 | McLuen | | |

(Continued)

OTHER PUBLICATIONS

International Search Report dated Oct. 13, 2017 issued in corresponding PCT/US2017/045255 application (2 pages).

*Primary Examiner* — Jacqueline T Johanas
(74) *Attorney, Agent, or Firm* — Millen, White, Zelano & Branigan, P.C.; William Nixon

(57) ABSTRACT

The present disclosure relates to an implant for insertion into an intervertebral space between a first vertebral member and a second vertebral member subsequent to a removal of a third vertebral member between the first vertebral member and the second vertebral member, the implant includes a first end, a second end and an implant body. The first end is to be secured to the first vertebral member. The second end is to be secured to the second vertebral member. The implant body is between the first end and the second end, wherein the implant body provides relative motion between the first end and second end.

1 Claim, 11 Drawing Sheets

(56) References Cited

U.S. PATENT DOCUMENTS

| | | | |
|---|---|---|---|
| 8,308,805 B2 | 11/2012 | Lynn et al. | |
| 8,313,529 B2* | 11/2012 | Lechmann | A61F 2/4425 |
| | | | 623/17.16 |
| 8,603,176 B2* | 12/2013 | Duplessis | A61F 2/442 |
| | | | 623/17.11 |
| 8,690,922 B2* | 4/2014 | Ritland | A61B 17/7011 |
| | | | 606/255 |
| 8,808,380 B2* | 8/2014 | Fox | A61B 17/8095 |
| | | | 623/17.13 |
| 9,149,366 B2* | 10/2015 | Prevost | A61F 2/4455 |
| 9,968,460 B2* | 5/2018 | Hadden, Jr. | A61F 2/4425 |
| 2002/0077702 A1* | 6/2002 | Castro | A61F 2/442 |
| | | | 623/17.16 |
| 2003/0083749 A1* | 5/2003 | Kuslich | A61F 2/44 |
| | | | 623/17.16 |
| 2004/0010254 A1* | 1/2004 | Cook | A61B 17/7059 |
| | | | 606/279 |
| 2004/0049279 A1* | 3/2004 | Sevrain | A61B 17/7059 |
| | | | 623/17.13 |
| 2004/0092929 A1* | 5/2004 | Zindrick | A61F 2/44 |
| | | | 606/247 |
| 2005/0125063 A1* | 6/2005 | Matge | A61F 2/442 |
| | | | 623/17.13 |
| 2005/0209694 A1* | 9/2005 | Loeb | A61B 17/1757 |
| | | | 623/17.11 |
| 2005/0228501 A1* | 10/2005 | Miller | A61F 2/44 |
| | | | 623/17.14 |
| 2005/0261773 A1* | 11/2005 | Ferree | A61F 2/4425 |
| | | | 623/17.16 |
| 2006/0064168 A1* | 3/2006 | Keller | A61F 2/44 |
| | | | 623/17.11 |
| 2006/0190079 A1 | 8/2006 | Istephanous et al. | |
| 2007/0093904 A1* | 4/2007 | Biedermann | A61B 17/7026 |
| | | | 623/17.13 |
| 2007/0123859 A1* | 5/2007 | Serhan | A61B 17/7071 |
| | | | 606/279 |
| 2007/0191953 A1* | 8/2007 | Trieu | A61F 2/442 |
| | | | 623/17.15 |
| 2007/0225806 A1* | 9/2007 | Squires | A61F 2/442 |
| | | | 623/17.11 |
| 2009/0062916 A1* | 3/2009 | Fox | A61F 2/4455 |
| | | | 623/17.16 |
| 2009/0112326 A1* | 4/2009 | Lehuec | A61F 2/441 |
| | | | 623/17.16 |
| 2010/0131067 A1* | 5/2010 | Metcalf, Jr. | A61B 5/0031 |
| | | | 623/17.16 |
| 2010/0204794 A1 | 8/2010 | Jarzem et al. | |
| 2010/0211106 A1* | 8/2010 | Bowden | A61B 17/7011 |
| | | | 606/260 |
| 2010/0292797 A1* | 11/2010 | Lindner | A61F 2/4405 |
| | | | 623/17.11 |
| 2011/0040334 A1* | 2/2011 | Kaes | A61F 2/28 |
| | | | 606/279 |
| 2011/0071636 A1* | 3/2011 | Tsuang | A61F 2/4425 |
| | | | 623/17.13 |
| 2011/0093075 A1* | 4/2011 | Duplessis | A61F 2/442 |
| | | | 623/17.16 |
| 2011/0098820 A1 | 4/2011 | Blackwell et al. | |
| 2011/0118794 A1* | 5/2011 | Pepper | A61B 17/7005 |
| | | | 606/305 |
| 2011/0178598 A1* | 7/2011 | Rhoda | A61F 2/44 |
| | | | 623/17.16 |
| 2012/0095561 A1 | 4/2012 | Voisard et al. | |
| 2012/0109307 A1 | 5/2012 | Drochner et al. | |
| 2012/0179258 A1* | 7/2012 | Glazer | A61F 2/4425 |
| | | | 623/17.16 |
| 2012/0323330 A1 | 12/2012 | Kueenzi et al. | |
| 2013/0123927 A1 | 5/2013 | Malandain | |
| 2014/0277484 A1* | 9/2014 | Prevost | A61F 2/4455 |
| | | | 623/17.16 |
| 2014/0277510 A1 | 9/2014 | Robinson et al. | |
| 2015/0209152 A1* | 7/2015 | Patterson | A61F 2/4455 |
| | | | 623/17.13 |
| 2016/0000575 A1* | 1/2016 | Sawyer | A61F 2/442 |
| | | | 623/17.16 |
| 2016/0030194 A1* | 2/2016 | Ledet | A61F 2/44 |
| | | | 623/17.16 |
| 2017/0071753 A1* | 3/2017 | Josse | A61F 2/4611 |
| 2017/0252070 A1* | 9/2017 | Tacca | A61B 17/7071 |

* cited by examiner

INTERVERTEBRAL IMPLANT

BACKGROUND

The spine is divided into four regions comprising the cervical, thoracic, lumbar, and sacrococcygeal regions. The cervical region includes the top seven vertebral members identified as C1-C7. The thoracic region includes the next twelve vertebral members identified as Th1-Th12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

As is known, various conditions and ailments may lead to damage of the spine, intervertebral discs and/or the vertebral members. The damage may result from a variety of causes including, but not limited to, events such as trauma, a degenerative condition, a tumor, or infection. Damage to the intervertebral discs and vertebral members can lead to pain, neurological deficit, and/or loss of motion.

Damage to a vertebral bone or a vertebral member may require removal of the vertebral body. This operation is known as a corpectomy. Following corpectomy, the resultant gap is generally filled by a weight bearing support, such as an autologous bone graft, or other devices known as a vertebral body replacement (VBR) cage. This helps to restore and maintain the proper spacing between the adjacent bones, and often provides a space for placement of graft material to span the adjacent bones in order to allow bone fusion to take place. Such replacement implants may be inserted to replace the damaged vertebral bodies and/or discs. The implants are intended to provide structure support and thus reduce or eliminate the pain and maintain neurological function. However, the resultant bone fusion may inevitably limit the range of motion between the indexed vertebral bodies. Although the current structural grafts and vertebral body replacement devices provide good weight support and induce arthrodesis, none of them can allow physiological movement between each of the vertebral segments involved. Therefore, a need remains for an implant that will overcome these shortfalls.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1A:
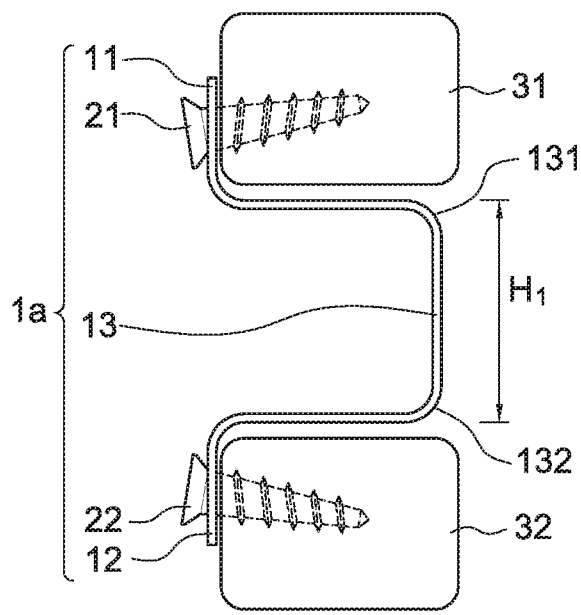
FIG. 1A illustrates a side view of an implant for spacing apart vertebral members in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

An implant for insertion into an intervertebral space between vertebral bodies to replace damages or diseased vertebral bodies can allow a relatively great range of motion similar to physiological movements of human spine.

Referring to the figures, wherein like numerals indicate like parts throughout the several views.

FIG. 1A illustrates an implant for spacing apart vertebral members in accordance with some embodiments of the present disclosure. Referring to FIG. 1A, an implant 1*a* is inserted into an intervertebral space between a vertebral member 31 and a vertebral member 32. The intervertebral space between the vertebral member 31 and the vertebral member 32 may be formed by removing a vertebral member (not shown in FIG. 1A) and/or intervertebral discs (not shown in FIG. 1A) between the vertebral member 31 and the vertebral member 32. The intervertebral space between the vertebral member 31 and the vertebral member 32 is formed subsequent to removal of a vertebral member (not shown in FIG. 1A) and/or intervertebral discs (not shown in FIG. 1A) between the vertebral member 31 and the vertebral member 32.

The implant 1*a* includes ends 11 and 12, an implant body 13 and securing elements 21 and 22.

The end 11 is secured or attached to the vertebral member 31 by the securing element 21. The end 12 is secured or attached to the vertebral member 32 by the securing element 22.

The implant body 13 is formed by a flexible and elastic material. The implant body 13 is formed by a bendable material. The implant body 13 is formed of material which can support body weight. The implant body 13 is formed by metal, plastic, polymer, or other suitable material. The implant body 13 is disposed between the vertebral member 31 and the vertebral member 32. The implant body 13 has an arcuate or angulate structure. Although it is not illustrated in FIG. 1A, it is contemplated that the implant body 13 has more arcuate, bending or angulate structure(s). The implant body 13 has a bend 131 adjacent to the vertebral member 31. The implant body 13 has a bend 132 adjacent to the vertebral member 32. The bend 131 and the bend 132 are formed on the same side of the implant body 13 (e.g. right side of the implant body). The bend 131 has an angulation from approximately 80° to approximately 100°. The bend 132 has an angulation from approximately 80° to approximately 100°. A distance $H_1$ substantially between the bend 131 and the bend 132 is from approximately 12 mm to 80 mm. A distance $H_1$ substantially between the bend 131 and the bend 132 is from approximately 15 millimeters (mm) to 65 mm. Although it is not illustrated in FIG. 1A, it is contemplated that the implant body 13 may include one or more bends on the same side as the bend 131. Although it is not illustrated in FIG. 1A, it is contemplated that the implant body 13 may include one or more bends on a side opposite the bend 131.

The implant body 13 is formed between the end 11 and the end 12. The implant body 13, the end 11 and the end 12 are formed in one piece. Each of the implant body 13, the end 11 and the end 12 may be formed separately as an independent segment and then be connected or integrated together. The implant body 13, the end 11 and the end 12 are formed by a same material. The implant body 13, the end 11 and the end 12 are formed by different materials.

Figure 1B:
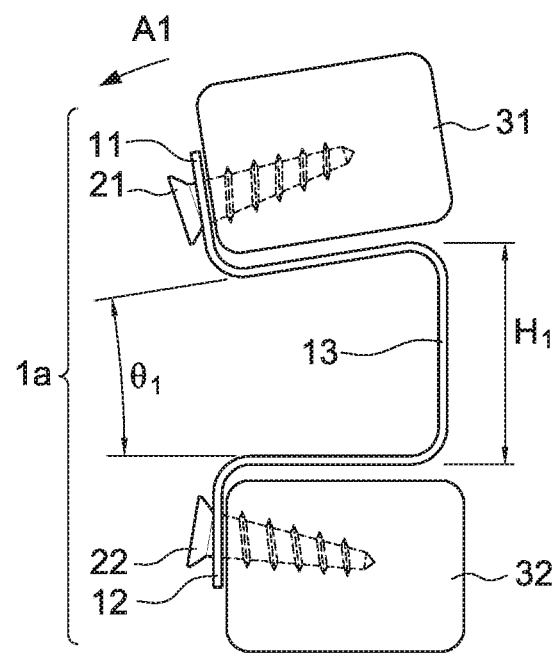
FIG. 1B illustrates an operation of the implant as shown in FIG. 1A.

FIG. 1B illustrates an operation of the implant 1*a* as shown in FIG. 1A. Referring to FIG. 1B, when a force or strength is applied from a direction as indicated by arrow A1 to the vertebral member 31 (e.g. when a spine is bending forward or bending in a plane other than sagittal plane or coronal plane), the implant body 13 is deformed. The deformation of the implant 13 changes a distance between the vertebral member 31 and the vertebral member 32. The deformation of the implant body 13 changes a distance between the end 11 and the end 12. A distance between the vertebral member 31 and the vertebral member 32 is less than the distance $H_1$. A distance between the end 11 and the end 12 is less than the distance $H_1$. The implant body 13 provides relative motion between the end 11 and the end 12. Deformation of the implant body 13 caused by the force or strength allow the vertebral member 31 to move relatively close to the vertebral member 32. The implant body 13 enables the end 11 to angulate relative to the end 12 by an angulation or angle $\theta_1$. The angulation $\theta_1$ has an angular value from approximately 0° to approximately 15°. The angulation $\theta_1$ has an angular value from approximately 5° to approximately 15°

Figure 1C:
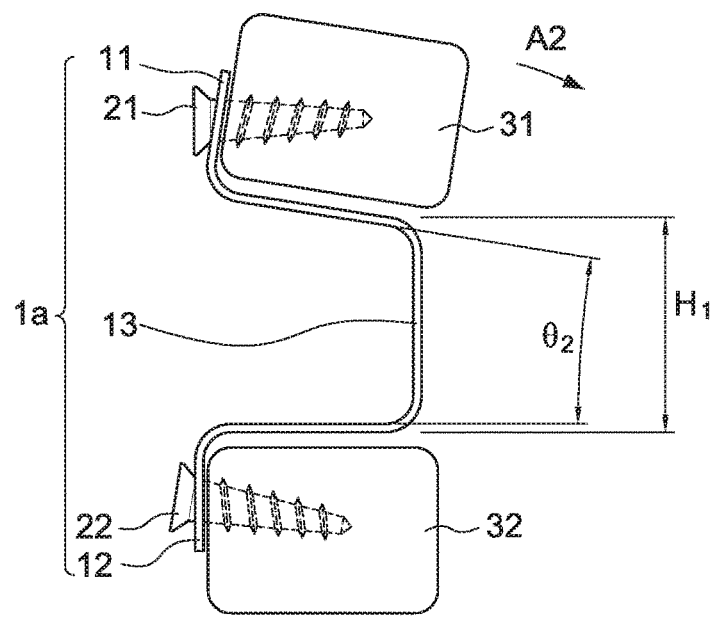
FIG. 1C illustrates an operation of the implant as shown in FIG. 1A.

FIG. 1C illustrates an operation of the implant 1*a* as shown in FIG. 1A. Referring to FIG. 1C, when a force or strength is applied from a direction as indicated by arrow A2 to the vertebral member 31 (e.g. when a spine is bending backward or bending in a plane other than sagittal plane or coronal plane), the implant body 13 is deformed. The deformation of the implant 13 changes a distance between the vertebral member 31 and the vertebral member 32. The deformation of the implant 13 changes a distance between the end 11 and the end 12. A distance between the vertebral member 31 and the vertebral member 32 is greater than the distance $H_1$. A distance between the end 11 and the end 12 is greater than the distance $H_1$. The implant body 13 provides relative motion between the end 11 and the end 12. Deformation of the implant body 13 caused by the force or strength allow the vertebral member 31 to move relatively away from the vertebral member 32. The implant body 13 enables the end 11 to angulate relative to the end 12 by an angulation or angle $\theta_2$. The angulation $\theta_2$ has an angular value from approximately 0° to approximately 15°. The angulation $\theta_2$ has an angular value from approximately 5° to approximately 15°.

Figure 1D:
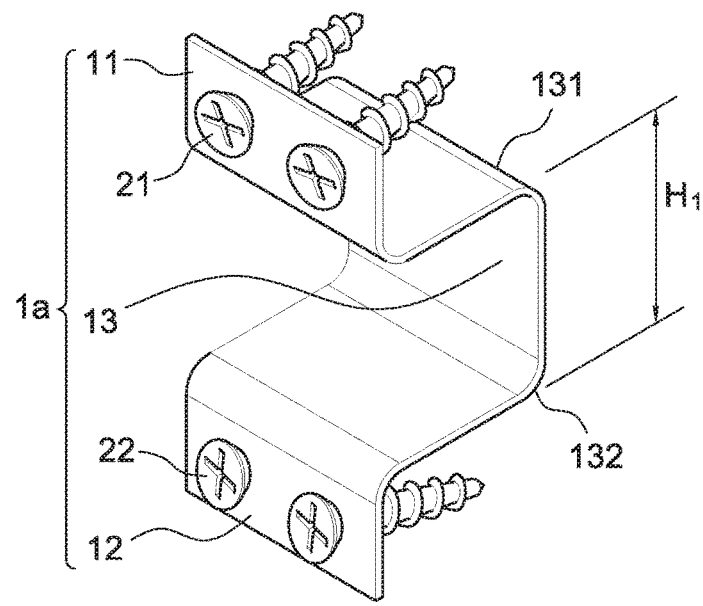
FIG. 1D illustrates a perspective view of an implant for spacing apart vertebral members in accordance with some embodiments of the present disclosure.

FIG. 1D illustrates a perspective view of an implant for spacing apart vertebral members in accordance with some embodiments of the present disclosure. Two securing elements 21 are used to secure the end 11 to the vertebral member 31. Two securing elements 22 are used to secure the end 12 to the vertebral member 32. It is contemplated that the arrangement of the securing elements 21 and 22, e.g. position, shape, amount, etc. thereof, can be varied in another embodiments of the present disclosure.

Figure 2A:
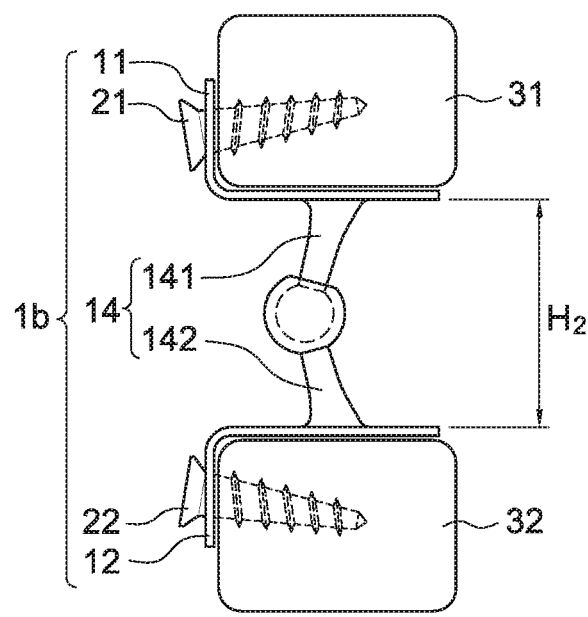
FIG. 2A illustrates an implant for spacing apart vertebral members in accordance with some embodiments of the present disclosure.

FIG. 2A illustrates an implant for spacing apart vertebral members in accordance with some embodiments of the present disclosure. Referring to FIG. 2A, an implant 1b is inserted into an intervertebral space between a vertebral member 31 and a vertebral member 32. The intervertebral space between the vertebral member 31 and the vertebral member 32 may be formed by removing a vertebral member (not shown in FIG. 2A) and/or intervertebral discs (not shown in FIG. 2A) between the vertebral member 31 and the vertebral member 32. The intervertebral space between the vertebral member 31 and the vertebral member 32 is formed subsequent to removal of a vertebral member (not shown in FIG. 2A) and/or intervertebral discs (not shown in FIG. 2A) between the vertebral member 31 and the vertebral member 32.

The implant 1b includes ends 11 and 12, an implant body 14 and securing elements 21 and 22.

The end 11 is secured or attached to the vertebral member 31 by the securing element 21. The end 12 is secured or attached to the vertebral member 32 by the securing element 22.

The implant body 14 has a body member 141 and a body member 142. The body member 141 is pivotably or rotabably connected to the body member 142. The body member 141 is pivotably or rotabably engaged with the body member 142. The implant body 14 may be formed by a flexible or elastic material. The implant body 14 may be formed by material having relatively higher abrasion resistance. The implant body 14 is formed by metal, plastic, polymer, ceramic, or other suitable material. The implant body 14 is disposed between the vertebral member 31 and the vertebral member 32. The body member 141 and the body member 142 form an arcuate or angulate structure. The body member 141 and the body member 142 form an arcuate or angulate structure which fit a curved configuration of human spine. The body member 141 and the body member 142 form a straight structure. A distance $H_2$ substantially between the vertebral member 31 and the vertebral member 32 is from approximately 12 mm to 80 mm. A distance $H_2$ substantially between the vertebral member 31 and the vertebral member 32 is from approximately 15 mm to 65 mm.

The implant body 14 is formed between the end 11 and the end 12. The body member 141 and the end 11 are formed in one piece. The body member 142 and the end 12 are formed in one piece. Each of the body member 141, the body member 142, the end 11 and the end 12 may be formed separately as an independent segment and then be connected or integrated together. The implant body 14, the end 11 and the end 12 are formed by a same material. The implant body 14, the end 11 and the end 12 are formed by different materials.

Figure 2B:
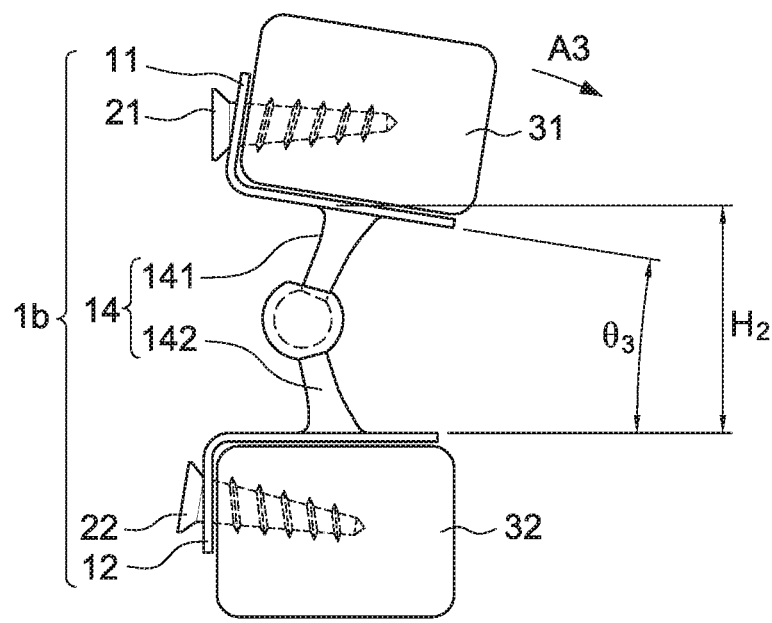
FIG. 2B illustrates an operation of the implant as shown in FIG. 2A.

FIG. 2B illustrates an operation of the implant 1b as shown in FIG. 2A. Referring to FIG. 2B, when a force or strength is applied from a direction as indicated by arrow A3 to the vertebral member 31 (e.g. when a spine is bending forward or backward or bending in a plane other than sagittal plane or coronal plane), the body member 141 moves relatively to the body member 142 to change a distance between the vertebral member 31 and the vertebral member 32. A relative motion between the body member 141 and the body member 142 changes a distance between the end 11 and the end 12. A distance between the vertebral member 31 and the vertebral member 32 is less than the distance $H_2$. A distance between the vertebral member 31 and the vertebral member 32 is less than the distance $H_2$ by approximately 1 to 3 mm. A distance between the end 11 and the end 12 is less than the distance $H_2$. A distance between the end 11 and the end 12 is greater than the distance $H_2$. The implant body 14 provides relative motion between the end 11 and the end 12. Pivotal motion of the implant body 14 caused by the force or strength allow a side of the vertebral member 31 to move relatively close to or away from the vertebral member 32. The implant body 14 enables the end 11 to angulate relative to the end 12 by an angulation or angle $\theta_3$. The angulation $\theta_3$ has an angular value from approximately 0° to approximately 30 The angulation θ3 has an angular value from approximately 10° to approximately 30° in sagittal plane. The angulation θ3 has an angular value from approximately 5° to approximately 10° in frontal plane or coronal plane.

Figure 3A:
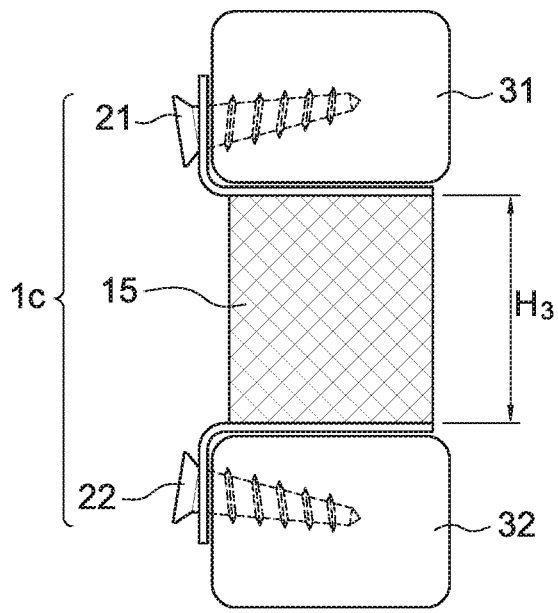
FIG. 3A illustrates an implant for spacing apart vertebral members in accordance with some embodiments of the present disclosure.

FIG. 3A illustrates an implant for spacing apart vertebral members in accordance with some embodiments of the present disclosure. Referring to FIG. 3A, an implant 1c is inserted into an intervertebral space between a vertebral member 31 and a vertebral member 32. The intervertebral space between the vertebral member 31 and the vertebral member 32 may be formed by removing a vertebral member (not shown in FIG. 3A) and/or intervertebral discs (not shown in FIG. 3A) between the vertebral member 31 and the vertebral member 32. The intervertebral space between the vertebral member 31 and the vertebral member 32 is formed subsequent to removal of a vertebral member (not shown in FIG. 3A) and/or intervertebral discs (not shown in FIG. 3A) between the vertebral member 31 and the vertebral member 32.

The implant 1c includes ends 11 and 12, an implant body 15 and securing elements 21 and 22.

The end 11 is secured or attached to the vertebral member 31 by the securing element 21. The end 12 is secured or attached to the vertebral member 32 by the securing element 22.

The implant body 15 is formed by a flexible or elastic material. The implant body 15 is formed by a deformable material. The implant body 15 is formed by plastic, rubber, polymer, or other suitable material. The implant body 15 is disposed between the vertebral member 31 and the vertebral member 32. A distance $H_3$ substantially between the vertebral member 31 and the vertebral member 32 is from approximately 12 mm to 80 mm. A distance $H_3$ substantially between the vertebral member 31 and the vertebral member 32 is from approximately 15 mm to 6 5 mm. A distance $H_3$ substantially between the end 11 and the end 12 is from approximately 12 mm to 80 mm. A distance $H_3$ substantially between the end 11 and the end 12 is from approximately 15 mm to 65 mm.

The implant body 15 is formed between the end 11 and the end 12. The implant body 15, the end 11 and the end 12 may be formed in one piece. Each of the implant body 15, the end 11 and the end 12 may be formed separately as an independent segment and then be connected or integrated together. The implant body 15, the end 11 and the end 12 are formed by a same material. The implant body 15, the end 11 and the end 12 are formed by different materials.

Figure 3B:
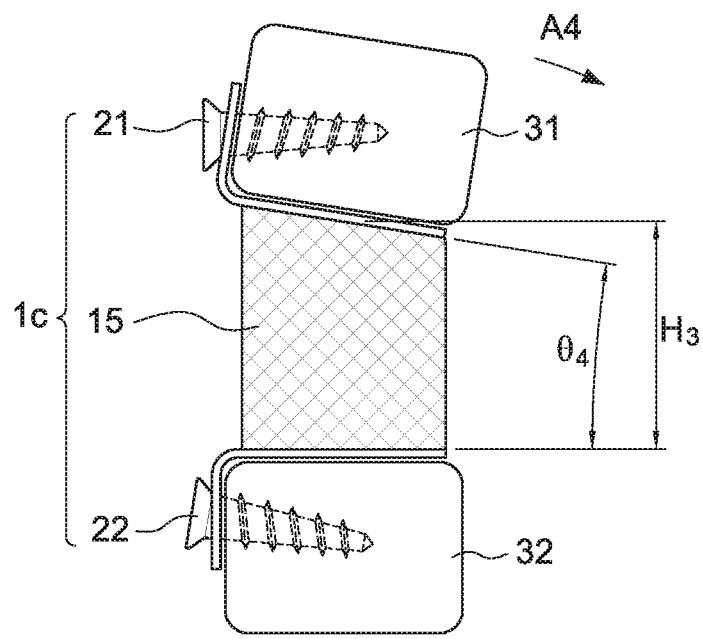
FIG. 3B illustrates an operation of the implant as shown in FIG. 3A.

FIG. 3B illustrates an operation of the implant 1c as shown in FIG. 3A. Referring to FIG. 3B, when a force or strength is applied from a direction as indicated by arrow A4 to the vertebral member 31 (e.g. when a spine is bending forward or backward or bending in a plane other than sagittal plane or coronal plane), the implant body 15 is deformed. Although it is not illustrated in FIG. 3B, another force or strength may be applied from a direction different from the arrow A4 to the vertebral member 31. The deformation of the implant 15 changes a distance between the vertebral member 31 and the vertebral member 32. The deformation of the implant body 15 changes a distance between the end 11 and the end 12. A distance between the vertebral member 31 and the vertebral member 32 is less than the distance $H_3$. A distance between the end 11 and the end 12 is less than the distance $H_1$. A distance between the vertebral member 31 and the vertebral member 32 is greater than the distance $H_3$. A distance between the end 11 and the end 12 is greater than the distance $H_3$. The implant body 15 provides relative motion between the end 11 and the end 12. Deformation of the implant body 15 caused by the force or strength allow the vertebral member 31 to move relatively close to or away from the vertebral member 32. The implant body 15 enables the end 11 to angulate relative to the end 12 by an angulation or angle $\theta_4$. The angulation $\theta_4$ has an angular value from 0° to approximately 20°.

Figure 4A:
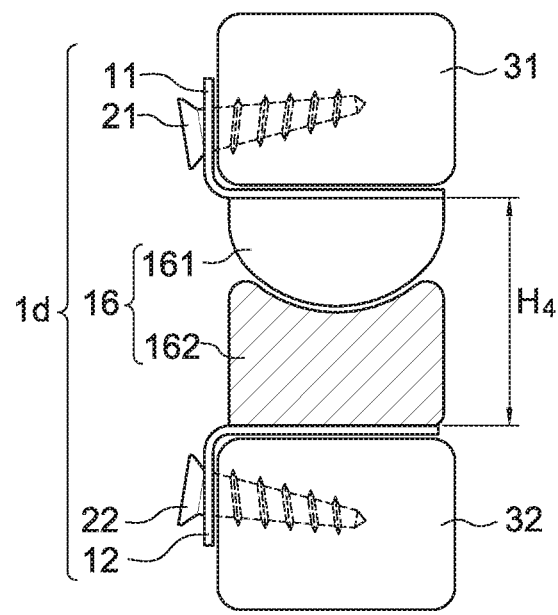
FIG. 4A illustrates an implant for spacing apart vertebral members in accordance with some embodiments of the present disclosure.

FIG. 4A illustrates an implant for spacing apart vertebral members in accordance with some embodiments of the present disclosure. Referring to FIG. 4A, an implant 1d is inserted into an intervertebral space between a vertebral member 31 and a vertebral member 32. The intervertebral space between the vertebral member 31 and the vertebral member 32 may be formed by removing a vertebral member (not shown in FIG. 4A) and/or intervertebral discs (not shown in FIG. 4A) between the vertebral member 31 and the vertebral member 32. The intervertebral space between the vertebral member 31 and the vertebral member 32 is formed subsequent to removal of a vertebral member (not shown in FIG. 4A) and/or intervertebral discs (not shown in FIG. 4A) between the vertebral member 31 and the vertebral member 32.

The implant 1d includes ends 11 and 12, an implant body 16 and securing elements 21 and 22.

The end 11 is secured or attached to the vertebral member 31 by the securing element 21. The end 12 is secured or attached to the vertebral member 32 by the securing element 22.

The implant body 16 has a body member 161 and a body member 162. The body member 161 is pivotably or rotatably connected to the body member 162. The body member 161 is pivotably or rotabably engaged with the body member 162. The body member 161 has a sepherical shape or contour. The body member 161 has a semisepherical shape or contour. The body member 162 has a recess to receive the body member 161. The implant body 16 may be formed by a flexible or elastic material. The implant body 16 may be formed by material having relatively higher abrasion resistance. The implant body 16 is formed by metal, plastic, polymer, ceramic or other suitable material. The implant body 16 is disposed between the vertebral member 31 and the vertebral member 32. The body member 141 and the body member 142 form an arcuate or angulate structure. A distance $H_4$ substantially between the vertebral member 31 and the vertebral member 32 is from approximately 12 mm to 80 mm. A distance $H_4$ substantially between the vertebral member 31 and the vertebral member 32 is from approximately 15 mm to 65 mm.

The implant body 16 is formed between the end 11 and the end 12. The body member 161 and the end 11 are formed in one piece. The body member 162 and the end 12 are formed in one piece. Each of the body member 161, the body member 162, the end 11 and the end 12 may be formed separately as an independent segment and then be connected or integrated together. The implant body 16, the end 11 and the end 12 are formed by a same material. The implant body 16, the end 11 and the end 12 are formed by different materials.

Figure 4B:
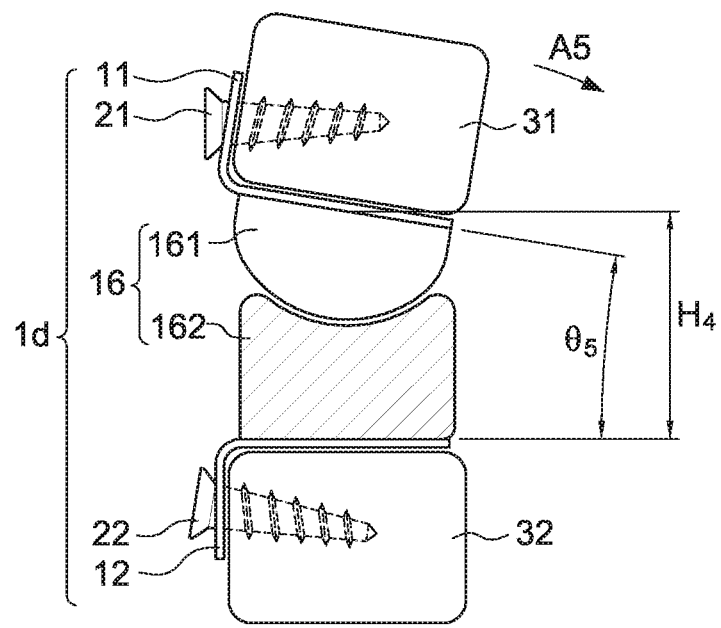
FIG. 4B illustrates an operation of the implant as shown in FIG. 4A.

FIG. 4B illustrates an operation of the implant 1d as shown in FIG. 4A. Referring to FIG. 4B, when a force or strength is applied from a direction as indicated by arrow A5 to the vertebral member 31 (e.g. when a spine is bending forward or backward or bending in a plane other than sagittal plane or coronal plane), the body member 161 moves relatively to the body member 162 to change a distance between the vertebral member 31 and the vertebral member 32. A relative motion between the body member 161 and the body member 162 changes a distance between the end 11 and the end 12. A distance between the vertebral member 31 and the vertebral member 32 is less than the distance $H_4$. A distance between the end 11 and the end 12 is less than the distance $H_4$. A distance between the end 11 and the end 12 is greater than the distance $H_4$. The implant body 16 provides relative motion between the end 11 and the end 12. Pivotal motion or rotation of the implant body 16 caused by the force or strength allow a side of the vertebral member 31 to move relatively close to or away from the vertebral member 32. The implant body 16 enables the end 11 to angulate relative to the end 12 by an angulation or angle $\theta_5$. The body member 161 is angulated relative to the body member 162 by an angulation or angle $\theta_5$. The angulation $\theta_5$ has an angular value from approximately 0° to approximately 30°. The angulation $\theta_5$ has an angular value from approximately 10° to approximately 30° in sagittal plane. The angulation $\theta_5$ has an angular value from approximately 5° to approximately 10° in frontal plane or coronal plane.

Figure 5A:
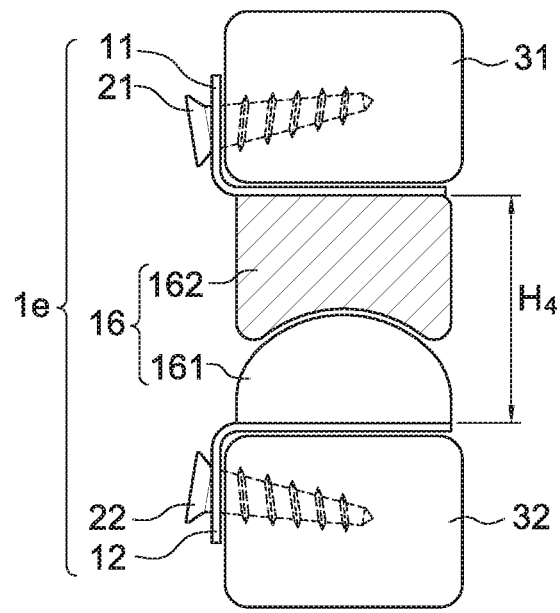
FIG. 5A illustrates an implant for spacing apart vertebral members in accordance with some embodiments of the present disclosure.

FIG. 5A illustrates an implant for spacing apart vertebral members in accordance with some embodiments of the present disclosure. Referring to FIG. 5A, an implant 1e is similar to the implant 1d as illustrated and described with reference to FIG. 4A, except that the position of the body member 161 and the position of the body member 162 are swapped.

Figure 5B:
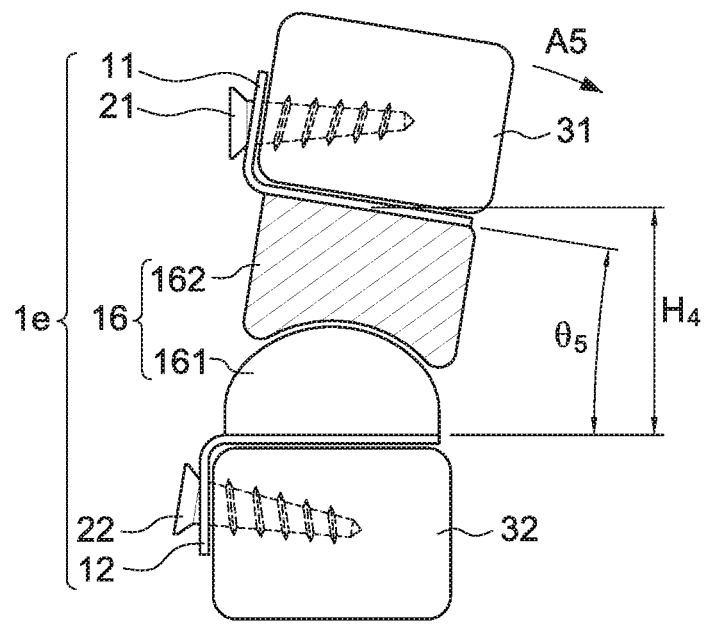
FIG. 5B illustrates an operation of the implant as shown in FIG. 5A.

FIG. 5B illustrates an operation of the implant 1e as shown in FIG. 5A. Referring to FIG. 5B, the operation of the implant 1e is similar to the operation of the implant 1d as illustrated and described with reference to FIG. 4B.

Figure 6A:
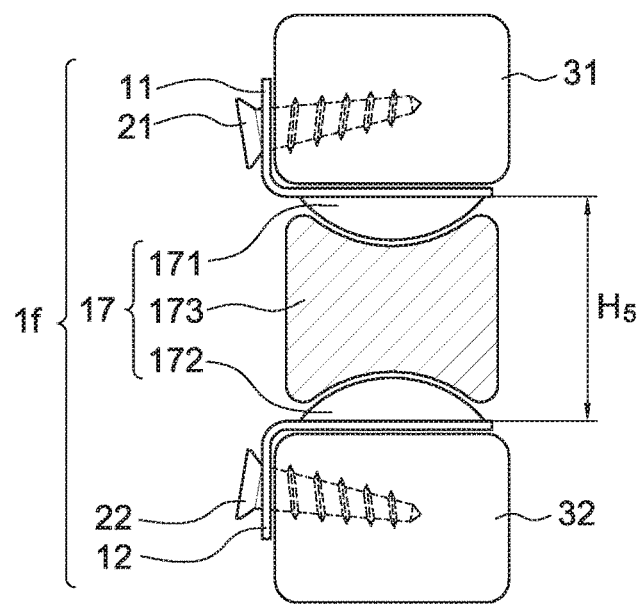
FIG. 6A illustrates an implant for spacing apart vertebral members in accordance with some embodiments of the present disclosure.

FIG. 6A illustrates an implant for spacing apart vertebral members in accordance with some embodiments of the present disclosure. Referring to FIG. 6A, an implant 1f is inserted into an intervertebral space between a vertebral member 31 and a vertebral member 32. The intervertebral space between the vertebral member 31 and the vertebral member 32 may be formed by removing a vertebral member (not shown in FIG. 6A) and/or intervertebral discs (not shown in FIG. 6A) between the vertebral member 31 and the vertebral member 32. The intervertebral space between the vertebral member 31 and the vertebral member 32 is formed subsequent to removal of a vertebral member (not shown in FIG. 6A) and/or intervertebral discs (not shown in FIG. 6A) between the vertebral member 31 and the vertebral member 32.

The implant 1ƒ includes ends 11 and 12, an implant body 17 and securing elements 21 and 22.

The end 11 is secured or attached to the vertebral member 31 by the securing element 21. The end 12 is secured or attached to the vertebral member 32 by the securing element 22.

The implant body 17 has a body member 171, a body member 172 and a body member 173. The body member 171 is pivotably or rotatably connected to the body member 173. The body member 171 is pivotably or rotabably engaged with the body member 173. The body member 172 is pivotably or rotatably connected to the body member 173. The body member 172 is pivotably or rotabably engaged with the body member 173. The body member 171 has a sepherical shape or contour. The body member 171 has a semisepherical shape or contour. The body member 172 has a sepherical shape or contour. The body member 172 has a semisepherical shape or contour. The body member 173 has a recess to receive the body member 171. The body member 173 has a recess to receive the body member 172. The body member 173 has two recesses to receive the body member 171 and the body member 172. The implant body 17 may be formed by a flexible or elastic material. The implant body 17 may be formed by material having relatively higher abrasion resistance. The implant body 17 is formed by metal, plastic, polymer, ceramic or other suitable material. The implant body 17 is disposed between the vertebral member 31 and the vertebral member 32. The body member 171 and the body member 173 form an arcuate or angulate structure. The body member 171 and the body member 173 form a straight structure. The body member 172 and the body member 173 form an arcuate or angulate structure. The body member 172 and the body member 173 form a straight structure. The body member 171, the body member 172 and the body member 173 form an arcuate or angulate structure. The body member 171, the body member 172 and the body member 173 form a straight structure. A distance $H_5$ substantially between the vertebral member 31 and the vertebral member 32 is from approximately 12 mm to 80 mm. A distance $H_5$ substantially between the vertebral member 31 and the vertebral member 32 is from approximately 15 mm to 65 mm.

The implant body 17 is formed between the end 11 and the end 12. The body member 171 and the end 11 are formed in one piece. The body member 172 and the end 12 are formed in one piece. Each of the body member 171, the body member 172, the body member 173, the end 11 and the end 12 may be formed separately as an independent segment and then be connected or integrated together. The implant body 17, the end 11 and the end 12 are formed by a same material. The implant body 17, the end 11 and the end 12 are formed by different materials.

Figure 6B:
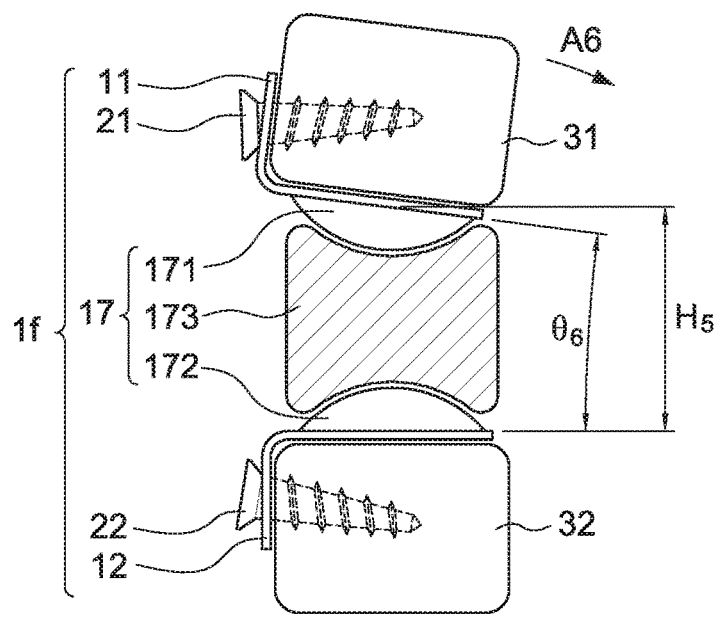
FIG. 6B illustrates an operation of the implant as shown in FIG. 6A.

FIG. 6B illustrates an operation of the implant 1ƒ as shown in FIG. 6A. Referring to FIG. 6B, when a force or strength is applied from a direction as indicated by arrow A6 to the vertebral member 31 (e.g. when a spine is bending forward or backward or bending in a plane other than sagittal plane or coronal plane), the body member 171 moves relatively to the body member 173 to change a distance between the vertebral member 31 and the vertebral member 32. A relative motion between the body member 171 and the body member 173 changes a distance between the end 11 and the end 12. A distance between the vertebral member 31 and the vertebral member 32 is less than the distance $H_5$. A distance between the end 11 and the end 12 is less than the distance $H_5$. A distance between the end 11 and the end 12 is greater than the distance $H_5$. The implant body 17 provides relative motion between the end 11 and the end 12. Pivotal motion or rotation of the implant body 17 caused by the force or strength allow a side of the vertebral member 31 to move relatively close to or away from the vertebral member 32. The implant body 17 enables the end 11 to angulate relative to the end 12 by an angulation or angle $\theta_6$. The body member 171 is angulated relative to the body member 173 by an angulation or angle $\theta_6$. The angulation $\theta_6$ has an angular value from approximately 0° to approximately 30°. The angulation $\theta_6$ has an angular value from approximately 10° to approximately 30° in sagittal plane. The angulation $\theta_6$ has an angular value from approximately 5° to approximately 10° in frontal plane or coronal plane.

Figure 6C:
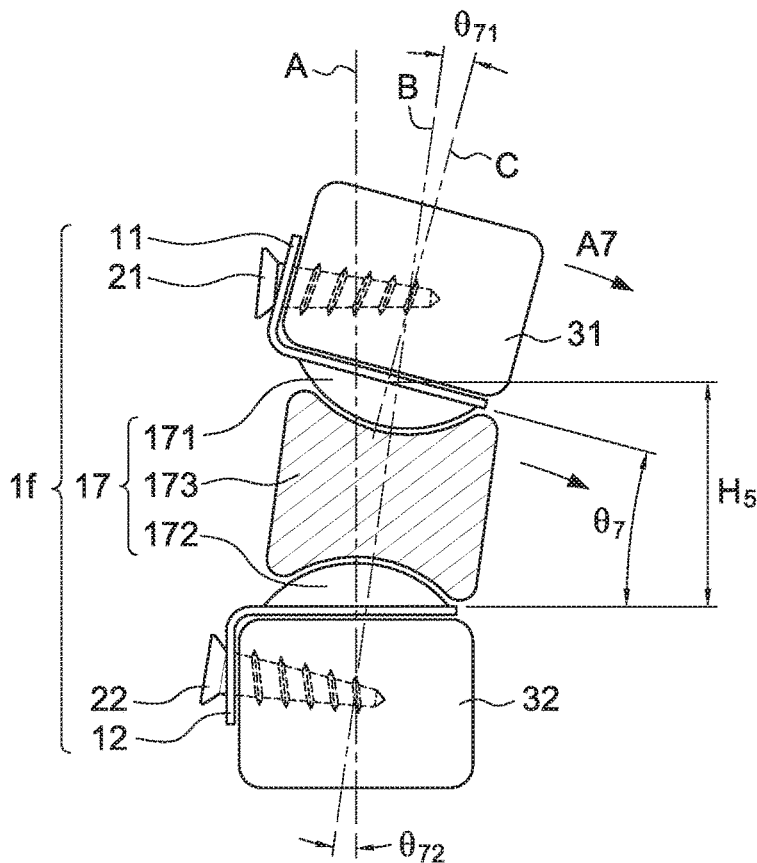
FIG. 6C illustrates another operation of the implant as shown in FIG. 6A.

FIG. 6C illustrates an operation of the implant 1ƒ as shown in FIG. 6A. Referring to FIG. 6C, when a force or strength is applied from a direction as indicated by arrow A7 to the vertebral member 31 (e.g. when a spine is bending forward or backward or bending in a plane other than sagittal plane or coronal plane), the body member 171 moves relatively to the body member 173 to change a distance between the vertebral member 31 and the vertebral member 32. When a force or strength is applied from a direction as indicated by arrow A7 to the vertebral member 31 (e.g. when a spine is bending forward or backward or bending in a plane other than sagittal plane or coronal plane), the body member 173 moves relatively to the body member 172 to change a distance between the vertebral member 31 and the vertebral member 32. A relative motion between the body member 171 and the body member 173 changes a distance between the end 11 and the end 12. A relative motion between the body member 173 and the body member 172 changes a distance between the end 11 and the end 12. A relative motion between the body member 171 and the body member 173 and a relative motion between the body member 173 and the body member 172 change a distance between the end 11 and the end 12. A distance between the vertebral member 31 and the vertebral member 32 is less than the distance $H_5$. A distance between the end 11 and the end 12 is less than the distance $H_5$. A distance between the end 11 and the end 12 is greater than the distance $H_5$. The implant body 17 provides relative motion between the end 11 and the end 12. Pivotal motion or rotation of the implant body 17 caused by the force or strength allow a side of the vertebral member 31 to move relatively close to or away from the vertebral member 32. The implant body 17 enables the end 11 to angulate relative to the end 12 by an angulation or angle $\theta_7$. The body member 171 is angulated relative to the body member 173 by an angulation or angle $\theta_{71}$. The angulation $\theta_{71}$ is formed between an axis B which passes center of the body member 173 and an axis C which passes center of the body member 171. The body member 173 is angulated relative to the body member 172 by an angulation or angle $\theta_{72}$. The angulation $\theta_{72}$ is formed between an axis B which passes center of the body member 173 and an axis A which passes center of the body member 172. The angulation $\theta_7$ may have an amount substantially the same as a sum of angulation $\theta_{71}$ and angulation $\theta_{72}$ The angulation $\theta_{71}$ has an angular value from approximately 0° to approximately 15°. The angulation $\theta_{72}$ has an angular value from approximately 0° to approximately 15°. The angulation $\theta_7$ has an angular value from approximately 0° to approximately 30°.

Figure 7:
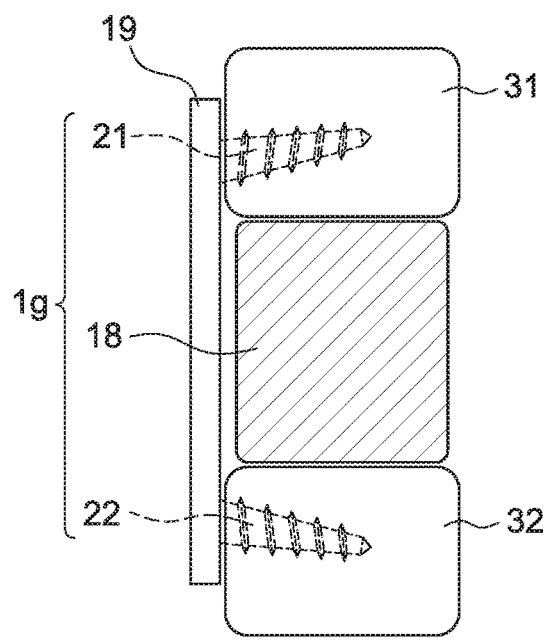
FIG. 7 illustrates an implant for spacing apart vertebral members in accordance with some embodiments of the present disclosure.

FIG. 7 illustrates an implant for spacing apart vertebral members in accordance with some embodiments of the present disclosure. Referring to FIG. 7, an implant 1g is inserted into an intervertebral space between a vertebral member 31 and a vertebral member 32. The intervertebral space between the vertebral member 31 and the vertebral member 32 may be formed by removing a vertebral member (not shown in FIG. 7) and/or intervertebral discs (not shown in FIG. 7) between the vertebral member 31 and the vertebral member 32. The intervertebral space between the vertebral member 31 and the vertebral member 32 is formed subsequent to removal of a vertebral member (not shown in FIG. 7) and/or intervertebral discs (not shown in FIG. 7) between the vertebral member 31 and the vertebral member 32.

The implant 1g includes a solid plate 19, a bone graft 18 and securing elements 21 and 22.

One end of the solid plate 19 is secured or attached to the vertebral member 31 by the securing element 21. One end of the solid plate 19 is secured or attached to the vertebral member 32 by the securing element 22.

The bone graft 18 is disposed between the vertebral member 31 and the vertebral member 32. The solid plate 19 which is fixed to the vertebral member 31 and the vertebral member 32 may constrain the relative motion or movement between the vertebral member 31 and the vertebral member 32.

Figure 8A:
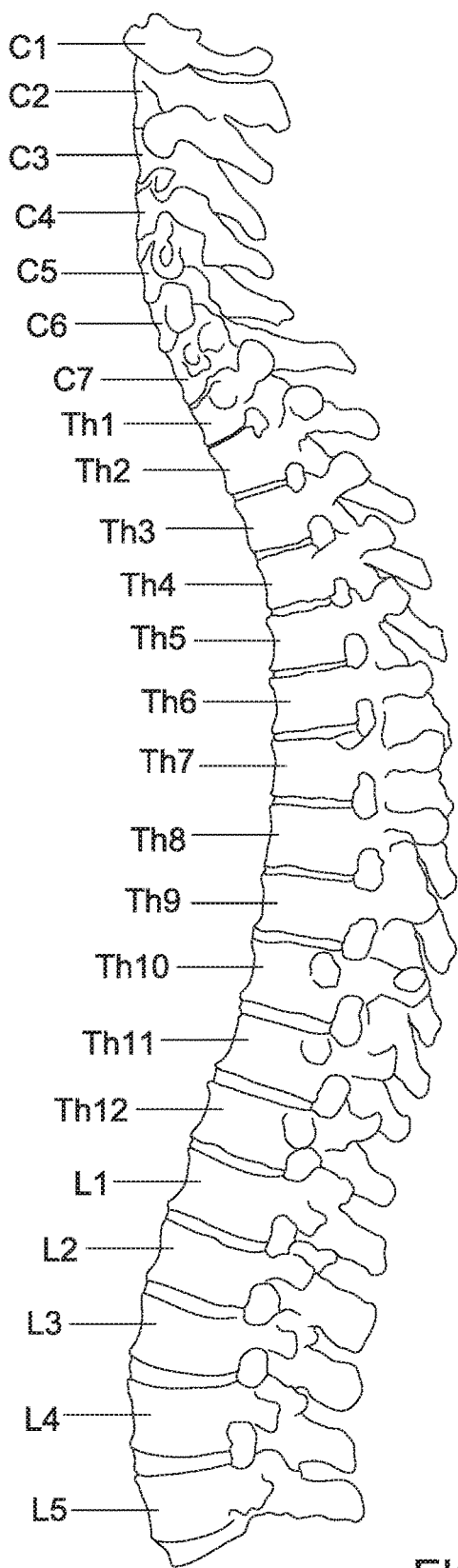
FIG. 8A illustrates a human spine in which the sacrococcygeal region is not shown for brevity, and only the cervical, thoracic and lumbar regions are illustrated.

FIG. 8A illustrates a human spine in which the sacrococcygeal region is not shown for brevity, and only the cervical, thoracic and lumbar regions are illustrated. The cervical region includes the top seven vertebral members identified as C1-C7. The thoracic region includes the next twelve vertebral members identified as Th1-Th12. The lumbar region includes five vertebral members L1-L5.

Figure 8B:
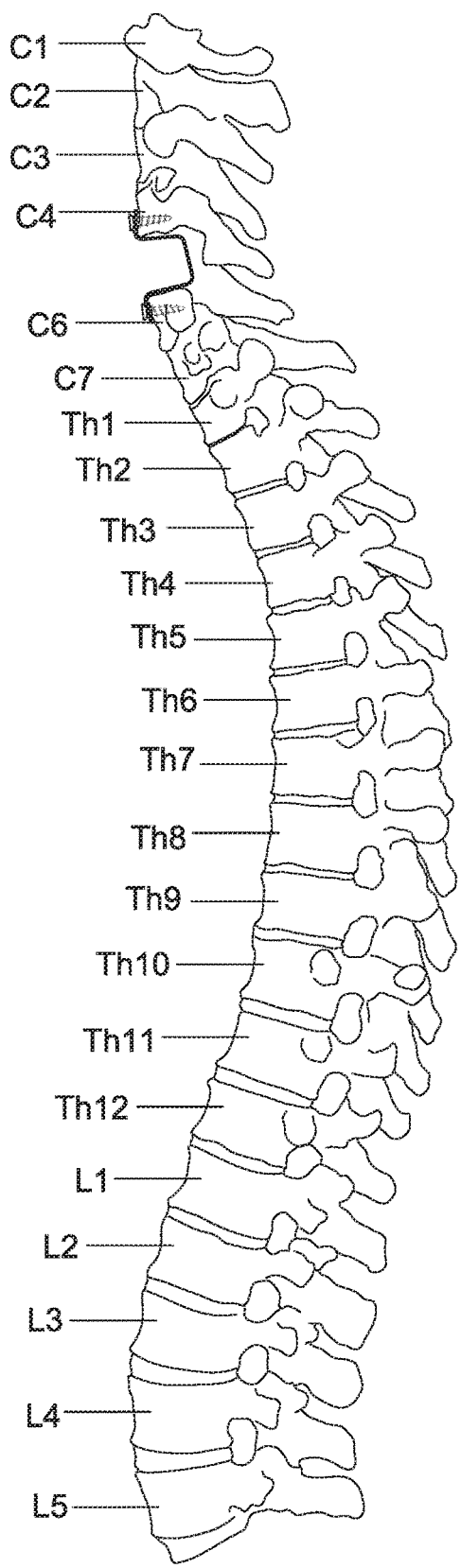
FIG. 8B illustrates an implant which replaces a part of a human spine as shown in FIG. 8A in accordance with some embodiments of the present disclosure.

FIG. 8B illustrates an implant which replaces a part of a human spine as shown in FIG. 8A in accordance with some embodiments of the present disclosure. Referring to FIG. 8B, a vertebral member C5 (and/or intervertebral discs) is removed and an implant 1a is inserted or mounted between the vertebral member C4 and the vertebral member C6. It is contemplated that any one of the implants 1b, 1c, 1d, 1e and 1f as described and illustrated with reference to FIG. 2A, FIG. 3A, FIG. 4A, FIG. 5A and FIG. 6A may be used to replace the implant 1a as shown in FIG. 8B to allow a relatively great range of motion similar to physiological movements of human spine.

Figure 8C:
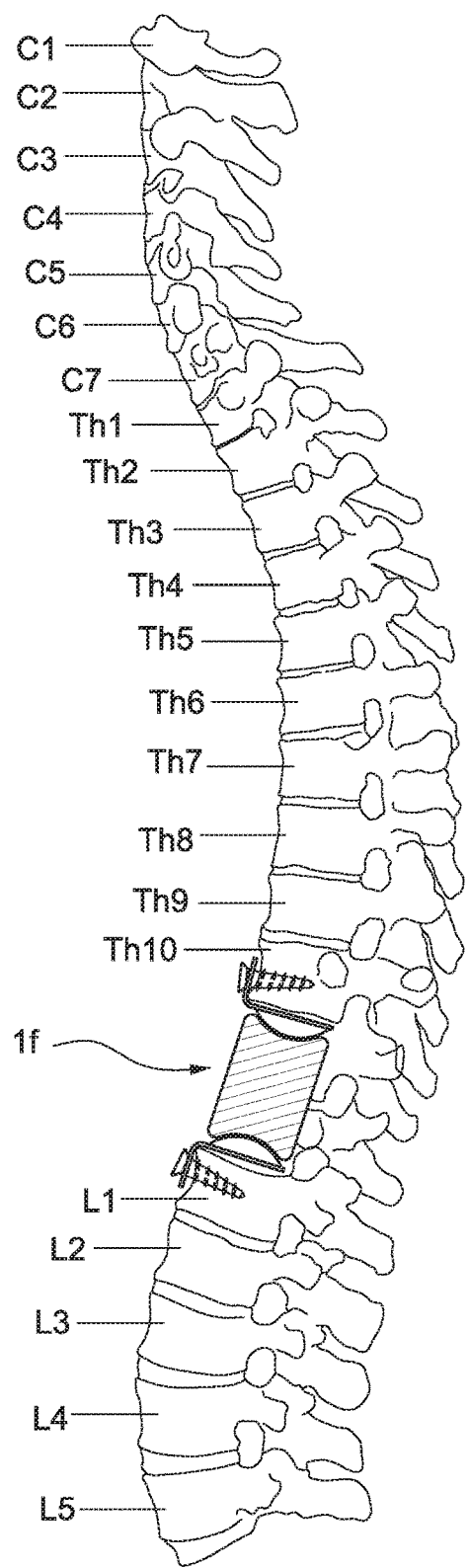
FIG. 8C illustrates an implant which replaces parts a human spine as shown in FIG. 8A in accordance with some embodiments of the present disclosure.

FIG. 8C illustrates an implant which replaces parts a human spine as shown in FIG. 8A in accordance with some embodiments of the present disclosure. Referring to FIG. 8C, the vertebral members Th11 and Th12 (and/or intervertebral discs) are removed and an implant 1f is inserted or mounted between the vertebral member Th10 and the vertebral member L1. It is contemplated that any one of the implants 1a, 1b, 1c, 1d and 1e as described and illustrated with reference to FIG. 1A, FIG. 2A, FIG. 3A, FIG. 4A, and FIG. 5A may be used to replace the implant 1f as shown in FIG. 8C to allow a relatively great range of motion similar to physiological movements of human spine.

In accordance with some embodiments of the present disclosure, an implant for insertion into an intervertebral space between a first vertebral member and a second vertebral member subsequent to a removal of a third vertebral member between the first vertebral member and the second vertebral member, the implant includes a first end, a second end and an implant body. The first end is to be secured to the first vertebral member. The second end is to be secured to the second vertebral member. The implant body is between the first end and the second end, wherein the implant body provides relative motion between the first end and second end.

In accordance with some embodiments of the present disclosure, an implant for insertion into an intervertebral space between a first vertebral member and second vertebral member subsequent to a removal of a third vertebral member between the first vertebral member and the second vertebral member, the implant includes a deformable implant body attached to the first vertebral member and the second vertebral member, wherein a distance between the first vertebral member and the second vertebral member is changed by the deformation of the deformable implant body.

In accordance with some embodiments of the present disclosure, an implant for insertion into an intervertebral space between a first vertebral member and second vertebral member subsequent to a removal of a third vertebral member between the first vertebral member and the second vertebral member, the implant includes a first implant body and a second implant body. The first implant body is secured to the first vertebral member. The second implant body is secured to the second vertebral member and pivotably connected to the first implant body, wherein the first implant body is enabled to angulate relative to the second implant body.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An implant for insertion into an intervertebral space between a first vertebra and a second vertebra subsequent to a removal of a third vertebra and intervertebral discs between the first vertebra and the second vertebra, the implant consisting of:
   a monolithic implant body formed by a rectangular plate, the rectangular plate having a height extending in a superior-inferior direction, a thickness extending in an anterior-posterior direction and a width extending in a lateral-medial direction, the height of the implant body being divided by bends into five straight segments, each bend spanning the width of the implant;
   four bone screws to secure the implant body to anterior surfaces of the first and second vertebrae;
   the five straight segments of the implant body include
      a first segment spanning from a superior free edge of the implant body to a first bend,
      a second segment spanning from the first bend to a second bend,
      a third segment spanning from the second bend to a third bend,
      a fourth segment spanning from the third bend to a fourth bend, and a fifth segment spanning from the fourth bend to an inferior free edge of the implant body, wherein the first, second, third, and fourth bends are 90 degree bends, wherein all five segments are smooth and flat, the first and fifth segments each have two holes to accommodate the bone screws and the second, third, and fourth segments have no openings therein, the first segment is configured to contact the anterior surface of the first vertebra, the second segment is configured to be placed adjacent an inferior endplate of the first vertebra, the third segment is configured to span the intervertebral spaces formed by the removal of the third vertebra and intervertebral discs, the fourth segment is configured to be placed adjacent a superior endplate of the second vertebra, and the fifth segment is configured to contact the anterior surface of the second vertebra, wherein the implant body is formed from a flexible material that allows relative movement between the first and second vertebrae, the range of motion between the second segment and the fourth segment is +/− 15 degrees from parallel, and wherein the height of the third segment along the superior-inferior direction is 20 mm to 80 mm.

* * * * *